(12) United States Patent
Harbin et al.

(10) Patent No.: US 7,449,546 B2
(45) Date of Patent: *Nov. 11, 2008

(54) METHOD FOR EXTENDING STORAGE OF GLUTATHIONE SOLUTIONS AND METHODS FOR TREATING PARKINSON'S DISEASE WITH SAID STORED GLUTATHIONE SOLUTIONS

(75) Inventors: Rod Harbin, Mountain Brook, AL (US); Larry Stephens, Homewood, AL (US)

(73) Assignee: Kromar Medical Corporation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/948,236

(22) Filed: Sep. 24, 2004

(65) Prior Publication Data
US 2005/0130905 A1    Jun. 16, 2005

Related U.S. Application Data

(63) Continuation of application No. 09/988,253, filed on Nov. 19, 2001, now Pat. No. 6,835,811.

(60) Provisional application No. 60/275,139, filed on Mar. 13, 2001.

(51) Int. Cl.
*A61K 38/00* (2006.01)
*C12P 21/02* (2006.01)

(52) U.S. Cl. ............................ 530/332; 514/2; 514/18; 514/21; 62/60; 62/62

(58) Field of Classification Search ................ 424/725
See application file for complete search history.

(56) References Cited

U.S. PATENT DOCUMENTS

2,702,799 A *  2/1955  Laufer et al. ................ 530/332
4,451,569 A     5/1984  Kobayashi et al.
5,736,139 A *  4/1998  Kink et al. ................ 424/164.1

OTHER PUBLICATIONS

Michell et al. Biomarkers and Parkinson's Disease; Brain (2004), 127, pp. 1693-1705.*
Samii et al. Parkinson's Disease; The Lancet, vol. 363, May 29, 2004, pp. 1783-1793.*
Kikkawa, et al., Change Due to Aging of Potassium Content, Carbonic Anhydrase, and Hemolysis of the Cold-Stored Human Erythrocyte, and Effect of Some Glucides, Thiol Compounds, and Adenosine-Triphosphate on Them, Jap. J. Pharmocology, (1959) 9, pp. 24-29.
G. Sechi; Reduced intravenous glutathione in the treatment of early parkinson's disease; Prog. In Neuro-Psychopharmacol. and Biol. Psychiat, 1996, vol. 20, pp. 1159-1170.

* cited by examiner

*Primary Examiner*—Patricia Leith
(74) *Attorney, Agent, or Firm*—Kramer & Amado, P.C.

(57) ABSTRACT

A method of storing solutions of reduced glutathione for extended periods of time, by dissolving reduced glutathione in an aqueous medium having a pH of between 5.0 and 8.0 to produce a reduced glutathione solution; reducing the temperature of the reduced glutathione solution to a predetermined temperature which is sufficiently low to prevent oxidative dimerization of glutathione without freezing the aqueous medium; and storing the reduced glutathione solution at the predetermined temperature.

5 Claims, 2 Drawing Sheets

METHOD FOR EXTENDING STORAGE OF GLUTATHIONE SOLUTIONS AND METHODS FOR TREATING PARKINSON'S DISEASE WITH SAID STORED GLUTATHIONE SOLUTIONS

This application is a continuation of U.S. application Ser. No. 09/988,253, filed on Nov. 19, 2001, now U.S. Pat. No. 6,835,811 which claims benefit of U.S. provisional Application No. 60/275,139, filed Mar. 13, 2001.

FIELD OF THE INVENTION

The invention relates to a method of storing reduced glutathione for extended periods of time. Normally, when a solution of reduced glutathione is stored, the percentage of biologically active glutathione which is present in solution undergoes a significant reduction over time. This is due to degradation of glutathione in solution. The current invention provides a method of storing reduced glutathione in solution for an extended period of time with little or no change in the concentration of the active ingredient.

This application claims the benefit of U.S. Provisional Application No. 60/275,139 entitled "EXTENDED STORAGE OF REDUCED GLUTATHIONE SOLUTIONS," filed on Mar. 13, 2001.

BACKGROUND ART

Glutathione, a tripeptide containing a free thiol group, is an important antioxidant. In preliminary research, dietary glutathione intake from fruit and raw vegetables has been associated with protection against some forms of cancer. Glutathione has also inhibited cancer in test tube and animal studies. In preliminary research, higher glutathione levels have also been associated with good health in older adults. In fact, glutathione levels appear to show a very strong correlation with life expectancy. The reduced glutathione (G-SH) molecule consists of three amino acids—glutamic acid, cysteine, and glycine—covalently joined end-to-end. The sulfhydryl group, which gives the molecule its electron-donating character, comes from the cysteine residue. Glutathione is present inside cells mainly in its reduced form.

Studies using intravenous or intramuscular glutathione have found it to be useful for preventing clot formation during operations; reducing the side effects and increasing the efficacy of chemotherapy drugs (particularly cisplatin in women with ovarian cancer); treating Parkinson's disease; reducing blood pressure in diabetics with high blood pressure; and increasing sperm counts in men with low sperm counts. Whether oral preparations are also effective is unknown at this time. A small study in eight patients with liver cancer using oral glutathione showed modest effects in women but not in men when given in a daily amount of 5,000 mg.

In the healthy cell, the concentration of oxidized glutathione (G-SS-G) is normally less than 10% of the total glutathione concentration. The ratio of reduced glutathione to oxidized glutathione appears to be an important indicator of the cell's health, and of its ability to resist oxidative stress. A reduction of reduced glutathione in a cell can trigger suicide of the cell by a process known as apoptosis.

Reduced glutathione (GSH) works as a potent anti-oxidant in the treatment of Parkinson's disease. According to research by Dr. David Perlmutter on alterations in glutathione levels, there seems to be both a clinical and neuropathological difference in Parkinson's disease patients treated with IV glutathione versus control groups. Dr. Perlmutter measured both GSH levels and oxidized glutathione (GSSG) levels in the brains of both Parkinson's patients and in the brains of patients in control groups. Glutathione levels were reduced approximately 40% and oxidized glutathione was increased approximately 29% in the patients with Parkinson's disease. This altered GSH/GSSG ratio in the brain may indicate that oxidative stress is a factor in brain cell death in Parkinson's disease. Therefore, treatment of Parkinson's disease with pure reduced glutathione may help to delay the progression of the disease.

Treatment of patients with lung diseases such as pulmonary fibrosis and emphysema with reduced glutathione is also useful. Reduced glutathione acts as an antioxidant, preventing oxidants in pollution and cigarette smoke from causing further damage to the lungs.

Unfortunately, reduced glutathione is not stable when subjected to long-term storage. The thiol group on the glutathione undergoes gradual oxidation to a disulfide, as shown:

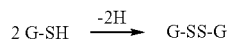

$$2 \text{ G-SH} \xrightarrow{-2\text{H}} \text{G-SS-G}$$

This reaction is catalyzed by the presence of molecular oxygen or of certain metal ions, such as $Fe^{+3}$, but it will proceed in aqueous solution in the absence of catalytic agents. As this reaction proceeds, there is a gradual reduction in the efficacy of the reduced glutathione solution against Parkinson's. In fact, if greater than 10% of the total glutathione in the reduced glutathione solution has undergone oxidation, the treatment may conceivably increase oxidative stress in the brain, exacerbating Parkinson's disease.

Thus, there is a long-felt need in the art for a method of storing aqueous solutions of reduced glutathione without allowing oxidation of the glutathione to a disulfide.

SUMMARY OF THE INVENTION

The current invention is directed toward extended storage of reduced glutathione in an aqueous medium having a pH of between 5.0 and 8.0, preferably between 6.2 and 7.8. The solution of reduced glutathione has a defined initial concentration. Even in the absence of oxidation catalysts such as molecular oxygen and/or metal ions, the concentration of reduced glutathione frequently undergoes a gradual reduction of between 10% and 15% of the initial concentration per month. It has been unexpectedly found that storing the reduced glutathione solution at a reduced temperature, which is above the freezing point of the solution and below 15° C., maintains the rate of reduced glutathione decay at between 0% and 5% of the defined initial concentration per month.

Thus, this invention provides a method for extended storage of reduced glutathione by dissolving a predetermined quantity of reduced glutathione in an aqueous medium having a pH of between 5.0 and 8.0 to produce a reduced glutathione solution having a predetermined initial concentration; reducing the temperature of the reduced glutathione solution to a predetermined temperature which is sufficiently low to prevent oxidative dimerization of glutathione without freezing the aqueous medium; and storing the reduced glutathione solution at the predetermined temperature.

DESCRIPTION OF THE PREFERRED EMBODIMENTS

Figure 1:
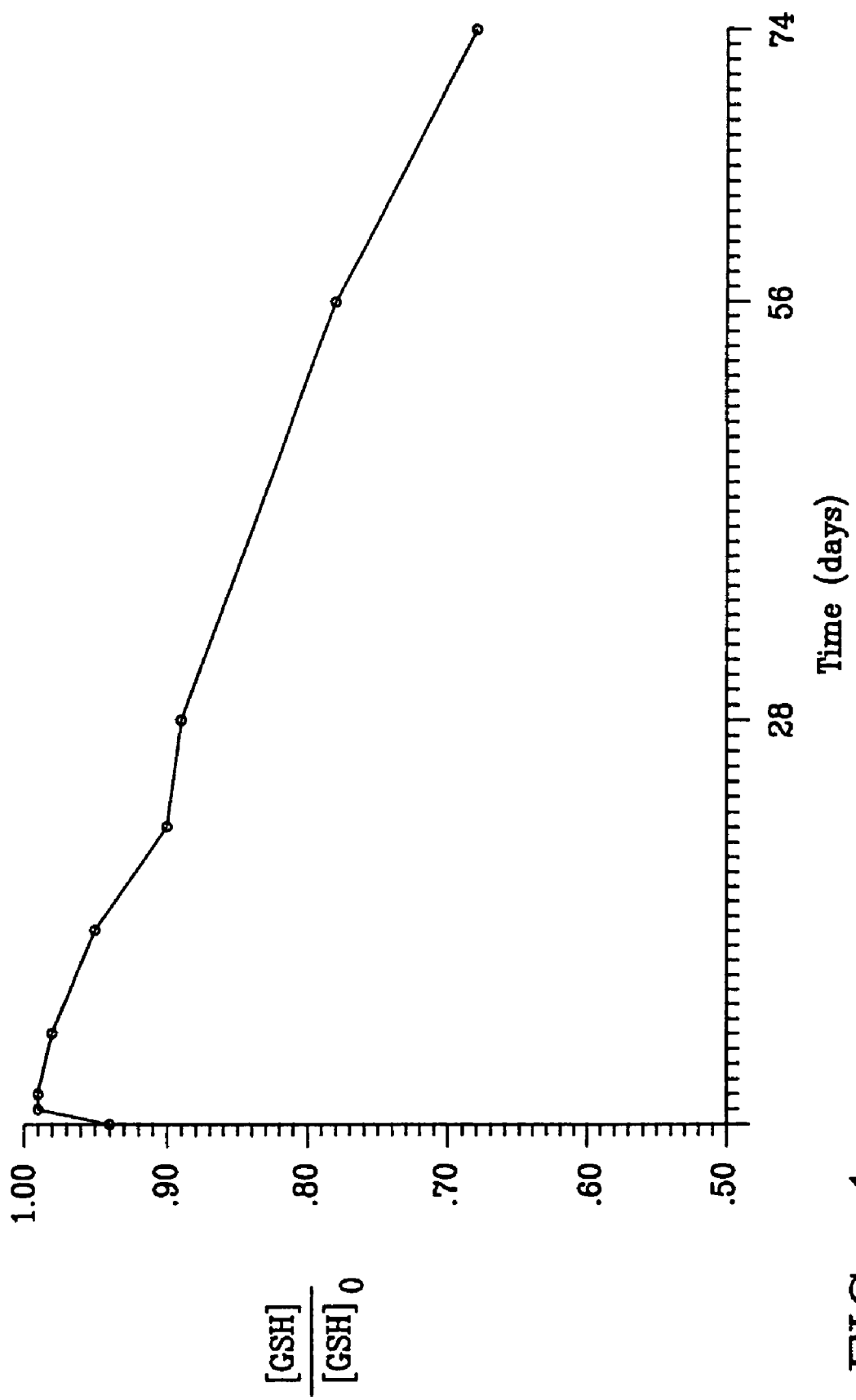
FIG. 1 shows the variation in the concentration of glutathione in an aqueous glutathione solution as a function of time, recorded at room temperature.

As previously noted, reduced glutathione (G-SH) undergoes an oxidative dimerization reaction, according to the chemical equation:

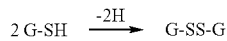

When the ratio of the actual concentration of reduced glutathione [G-SH] at time t (recorded in Table 1) to the initial concentration of reduced glutathione $[G\text{-}SH]_o$ in a solution which is free of oxidation catalysts, such as metal ions and/or molecular oxygen, is plotted as a function of time (see FIG. 1), the ratio $[G\text{-}SH]/[G\text{-}SH]_o$ decreases with time in a linear fashion with a temperature-dependent slope K. It is important that solutions of reduced glutathione be used before the concentration of the oxidized disulfide of glutathione builds up to a significant extent, particularly when treating Parkinson's disease. Otherwise, administration of a reduced glutathione solution will fail to compensate for the altered GSH/GSSG ratio in the brain of Parkinson's patients. Preferably, the reduced glutathione solution is administered while the concentration of reduced glutathione is still at least 90% of the initial reduced glutathione concentration. As a result, reduced glutathione cannot be safely stored in aqueous solution at room temperature for longer than three weeks, even in the absence of oxidation catalysts (see Table 1).

The rate at which the concentration of reduced glutathione in solution declines is dependent in large part on the rate constant k for glutathione oxidation:

$$2\,G\text{-}SH \xrightarrow{k} G\text{-}SS\text{-}G + 2H$$

The rate constant for a reaction is well known to be temperature dependent, according to the Arrhenious equation:

$k = A\exp(-E_a/RT)$ where $E_a$ is the activation energy of the reaction, R is the universal gas constant, T is temperature, and A is a temperature-independent preexponential factor.

TABLE 1

Effect of Long-Term Storage at 25° C. on
Reduced Glutathione Concentration

| [G-SH]/[G-SH]₀ | Time (days) |
|---|---|
| 0.94 | 1 |
| 0.99 | 2 |
| 0.99 | 3 |
| 0.98 | 7 |
| 0.95 | 14 |
| 0.90 | 21 |
| 0.89 | 28 |
| 0.78 | 56 |
| 0.68 | 74 |

Thus, for most reactions, the rate constant k increases with increasing temperature. Therefore, it should be possible to slow the rate of glutathione oxidative dimerization down by decreasing the temperature. A typical reaction rate having an activation energy of roughly 50 kJ mol$^{-1}$ changes by a factor of two for a 10° C. temperature change. Therefore, it can be anticipated that the rate of reaction for glutathione dimerization can be decreased by a factor of four by lowering the temperature of the solution from room temperature by about 20° C.

However, it has unexpectedly been found that the rate of glutathione dimerization is not simply reduced by lowering the solution temperature by 20° C. from room temperature. Rather, the dimerization of glutathione is essentially stopped (see Table 2), allowing the storage of the reduced glutathione solution for periods of time of significantly greater than four months.

TABLE 2

Effect of Long-Term Storage at 5° C. on
Reduced Glutathione Concentration

| [G-SH]/[G-SH]₀ | Time (days) |
|---|---|
| 1.02 | 1 |
| 1.01 | 2 |
| 1.01 | 3 |
| 1.02 | 7 |
| 1.00 | 14 |
| 0.99 | 21 |
| 1.02 | 28 |
| 1.00 | 56 |
| 1.00 | 84 |
| 0.98 | 112 |

Additionally, dramatic reductions in the rate of oxidative dimerization of glutathione can be achieved through storage of a reduced glutathione solution at a temperature which is above the freezing point of the aqueous medium and below 15° C. Under these conditions, the rate of glutathione dimerization is dramatically reduced, with the concentration of reduced glutathione decreasing at a rate of between 0% and 5% of the initial reduced glutathione concentration per month.

Thus, this invention provides a method for extended storage of reduced glutathione in solution, by dissolving a predetermined quantity of reduced glutathione in an aqueous medium to produce a reduced glutathione solution having a predetermined initial concentration; reducing the temperature of the reduced glutathione solution to a predetermined temperature which is sufficiently low to slow the rate of oxidative dimerization of glutathione without freezing the aqueous medium; and storing the reduced glutathione solution at the predetermined temperature. The aqueous medium is preferably a solution of reduced glutathione at a concentration of between 10 mg/ml and 400 mg/ml having a pH of between 5.0 and 8.0. The solution may additionally comprise a buffer, such as octylammonium orthophosphate, to control the pH of the solution. It is preferred that the solution be stored under a non-oxidizing atmosphere which is free of molecular oxygen (i.e., nitrogen, argon, or a vacuum), and that the solution be prepared using distilled water which is free of metallic ions. The solution may be stored in single-dose or multi-dose ampoules or vials. If the solution is stored in multi-dose ampoules or vials, it is preferred that the ampoules or vials should be sealed with an elastomeric septum. The solution can then be withdrawn by syringe through the septum, while minimizing access of atmospheric oxygen to the reduced glutathione solution.

Additionally, this invention provides a method for treating a patient with Parkinson's disease with reduced glutathione while minimizing the risk of oxidative stress on the brain. This is done by dissolving a predetermined quantity of reduced glutathione in an aqueous medium having a pH of between 5:0 and 8.0, preferably between 6.2 and 7.8, to produce a reduced glutathione solution; storing the reduced glutathione solution at the predetermined temperature; and administering the reduced glutathione to the patient with Parkinson's disease. This eliminates further deleterious effect on the health of brain cells from increases in the level of oxidized glutathione relative to reduced glutathione. The glutathione solution may be administered intravenously, by intramuscular injection, by subcutaneous injection, or orally. The glutathione solution may also be administered orally, in either a liquid form or as the contents of a liquid-filled capsule. If desired, agar or gelatin may be added to the aqueous contents of the capsule to provide additional viscosity to the solution. The shell of the capsule degrades in the small intestine, releasing the glutathione. It is also possible to add sufficient agar or gelatin to the solution of reduced glutathione to convert the reduced glutathione to a self-sustaining gel. This gel may then be swallowed orally, or inserted rectally and used as a suppository. Alternatively, in one embodiment, the reduced glutathione solution may be stored under an inert atmosphere in a spray bottle having a sealed opening. The opening of the spray bottle may then be opened to the atmosphere with a pin or similar implement, and the contents of the spray bottle may then be sprayed into the nasal or oral cavity. The glutathione may then be transported across the patient's mucous membranes into the bloodstream.

Finally, this invention provides a method for treating a patient with emphysema with reduced glutathione. This is done by dissolving a predetermined quantity of reduced glutathione in an aqueous medium having a pH of between 5.0 and 8.0, preferably between 6.2 and 7.8, to produce a reduced glutathione solution; storing the reduced glutathione solution at the predetermined temperature; and administering the reduced glutathione to the patient with emphysema. The glutathione solution may be administered by any of the methods described above for treatment of Parkinson's; however, it is preferred to provide the reduced glutathione solution under an inert atmosphere in a spray bottle having a sealed opening. The opening of the spray bottle may then be opened to the atmosphere, and the contents of the spray bottle may then be sprayed into the nasal cavity. This provides the most rapid access of reduced glutathione to the respiratory surfaces.

COMPARATIVE EXAMPLE

A reduced glutathione solution containing reduced glutathione at an initial concentration of 180 mg/ml and octylammonium orthophosphate at a concentration of 0.005M was prepared. The solution had a pH of 6.4. This solution was stored at room temperature (25° C.) for 74 days. The concentration of reduced glutathione exhibited a decrease over time, with a steady rate of decay of between 10% and 12% of the initial reduced glutathione concentration per month (FIG. 1). Within three weeks, the concentration of reduced glutathione had decreased to 90% of its initial value (Table 1). This decrease is sufficient to render the solution of questionable value for the treatment of Parkinson's disease.

EXAMPLE

Figure 2:
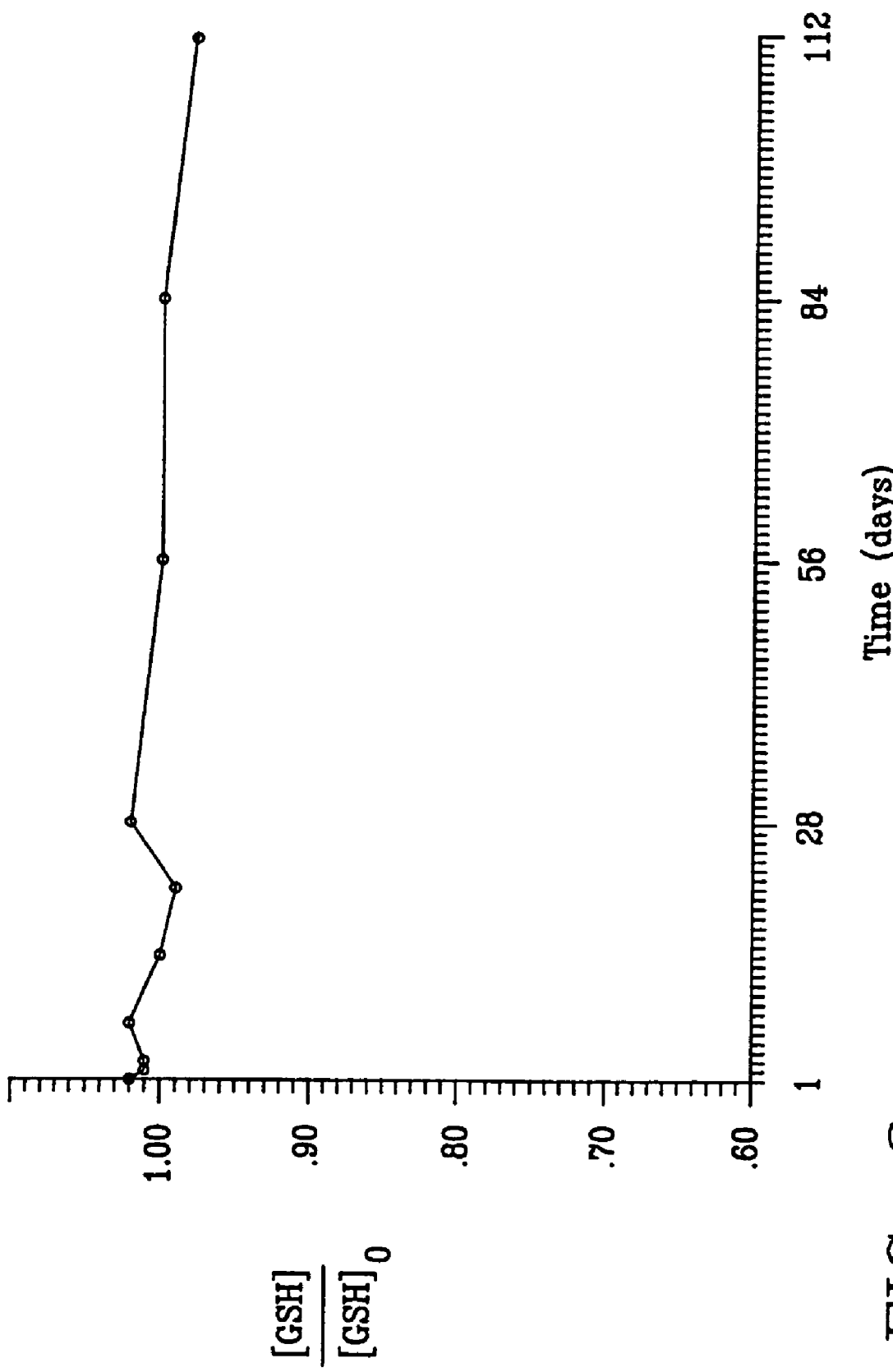
FIG. 2 shows the variation in the concentration of glutathione in an aqueous glutathione solution as a function of time, recorded under conditions of refrigeration.

A reduced glutathione solution containing reduced glutathione at an initial concentration of 189 mg/ml and octylammonium orthophosphate at a concentration of 0.005M was prepared. The solution had a pH of 6.4. This solution was stored at 5° C., and the concentration of reduced glutathione was monitored for four months (Table 2). Within experimental error, the concentration of reduced glutathione exhibited no decrease over time (FIG. 2).

What is claimed is:

1. A method for extended storage of reduced glutathione in solution, comprising the steps of:
   a) dissolving a predetermined quantity of reduced glutathione in an aqueous medium free of metal ions, said medium having a pH of between 5.0 and 8.0 to produce a reduced glutathione solution having a predetermined initial concentration $[A]_o$, where the initial concentration $[A]_o$ is between 10 mg/ml and 400 mg/ml;
   b) reducing the temperature of the reduced glutathione solution to a predetermined temperature which is sufficiently low to prevent oxidative dimerization of glutathione without freezing the aqueous medium, said predetermined temperature being below 15° C.; and
   c) storing the reduced glutathione solution at the predetermined temperature for a period of from 14 to 112 days.

2. A method for preparing a reduced glutathione composition, comprising the steps of:
   a) dissolving a predetermined quantity of reduced glutathione in an aqueous medium free of metal ions, said medium having a pH of between 5.0 and 8.0 to produce a reduced glutathione solution having a predetermined initial concentration $[A]_o$, wherein, when the ratio $[A]/[A]_o$, where $[A]$ is the actual glutathione concentration at time t, is plotted as a function of time t, the concentration of reduced glutathione decreases over time in a linear fashion with a temperature-dependent slope; and
   b) storing the reduced glutathione solution at a predetermined temperature which is above the freezing point of the solution and below 15° C., so as to maintain a rate of change of reduced glutathione concentration at between 0% and 5% of the predetermined initial concentration per month,
   where the initial concentration of reduced glutathione is between 10 mg/ml and 400 mg/ml.

3. A method for preparing a reduced glutathione composition, comprising the steps of:
   a) dissolving a predetermined quantity of reduced glutathione in an aqueous medium free of metal ions, said medium having a pH of between 5.0 and 8.0 to produce a reduced glutathione solution having a predetermined initial concentration, wherein the concentration of reduced glutathione decays over time in a linear fashion;
   b) storing the reduced glutathione solution at a predetermined temperature which is above the freezing point of the solution and below 15° C., so as to maintain a rate of change of reduced glutathione concentration at between 0% and 5% of the predetermined initial concentration per month,
   where the initial concentration of reduced glutathione is between 10 mg/ml and 400 mg/ml.

4. A method for handling and administering reduced glutathione, comprising the steps of:
   a) dissolving a predetermined quantity of reduced glutathione in an aqueous medium having a pH of between 5.0 and 8.0 to produce a reduced glutathione solution having a predetermined initial concentration, wherein the concentration of reduced glutathione decays over time in a linear fashion;
   b) maintaining a rate of change of reduced glutathione concentration at between 0% and 5% of the predetermined initial concentration per month by storing the reduced glutathione solution at a predetermined temperature which is above the freezing point of the solution and below 15° C., so as to maintain a rate of change of reduced glutathione concentration at between 0% and 5% of the predetermined initial concentration per month;

where the initial concentration of reduced glutathione is between 10 mg/ml and 400 mg/ml;

and further comprising a step of administering the reduced glutathione solution to a patient with Parkinson's disease.

5. A method for treating a patient with Parkinson's disease with reduced glutathione, comprising the steps of:
a) dissolving a predetermined quantity of reduced glutathione in an aqueous medium free of metal ions, said medium having a pH of between 5.0 and 8.0 to produce a reduced glutathione solution having a predetermined initial concentration $[A]_o$, where the initial concentration $[A]_o$ is between 10 mg/ml and 400 mg/ml;
b) reducing the temperature of the reduced glutathione solution to a predetermined temperature which is sufficiently low to prevent oxidative dimerization of glutathione without freezing the aqueous medium, said predetermined temperature being below 15° C.;
c) storing the reduced glutathione solution at the predetermined temperature for a period of from 14 to 112 days; and
d) administering the stored reduced glutathione of part (c) to the patient with said Parkinson's disease.

* * * * *